United States Patent [19]

Merry et al.

[11] Patent Number: 4,946,460
[45] Date of Patent: Aug. 7, 1990

[54] APPARATUS FOR CRYOSURGERY

[75] Inventors: Nir Merry, Berkeley; Michael Smidebush, Concord, both of Calif.

[73] Assignee: Cryo Instruments, Inc., Berkeley, Calif.

[21] Appl. No.: 343,950

[22] Filed: Apr. 26, 1989

[51] Int. Cl.$^5$ .............................................. A61B 17/36
[52] U.S. Cl. .................................... 606/24; 606/21
[58] Field of Search ................................ 606/20–26

[56] References Cited
U.S. PATENT DOCUMENTS 3,398,738  8/1968  Lamb et al. ............................ 606/23
3,782,386  1/1974  Barger et al. .......................... 606/23
3,971,383  7/1976  van Gerven ........................ 128/303.1
4,202,336  5/1980  van Gerven ............................ 606/21
4,211,231  7/1980  Rzasa ................................. 128/303.1
4,823,790  4/1989  Alperovich et al. ................. 606/24

Primary Examiner—Max Hindenburg
Attorney, Agent, or Firm—Sherman and Shalloway

[57] ABSTRACT

An apparatus for cryosurgery having the ability to precisely control the rate and degree of freezing of diseased tissue by means of a cryoprobe having a plurality of removable cryotips, and a compensating temperature control system operably associated with the cryoprobe.

8 Claims, 3 Drawing Sheets

APPARATUS FOR CRYOSURGERY

BACKGROUND OF THE INVENTION

1. Field of the Invention

The present invention relates generally to cryosurgical devices. More particularly, the invention concerns a surgical apparatus that has the ability to control the freezing process both in space and in time by means of a cryoprobe having a plurality of removable cryotips, and a compensating temperature control system operably associated with the cryoprobe.

2. Discussion of Prior Art

Cryosurgery is a surgical procedure that uses freezing temperatures to destroy tissue. James Arnott, an English physician, was the first to introduce this method in 1865 for treatment of cancer of the skin. Between 1920 and 1940, the commercialization of liquid air led a number of surgeons to employ freezing to accomplish the destruction of nondesirable tissue. By 1930 the first monograph on the method was published (Lortat-Jacobs and Solente, 1930).

Modern cryosurgery started with the work of a New York surgeon, I. Cooper, who in 1961 developed a new apparatus for cryosurgery. This apparatus consisted of a hollow metal tube which was vacuum insulated, except at the tip, through which liquid nitrogen was circulated. Cooper was able to localize the freezing and, thereby, treat the tissue in a controlled way. The method was used first for treatment of Parkinsonism, and later extended to the destruction of non desirable tissue in other areas, such as dermatology, proctology, gynecology. The applications of cryosurgery are numerous and have been described in several texts and review papers, (Rand et al., 1968; Ablin 1980; Gage 1982; Zacarian, 1985; Gage, 1988; Gage and Torre, 1988; Onvk and Rubinsky, 1988).

Until recently there were two major problems that hindered the efficient application of cryosurgery to the treatment of cancer and other nondesirable tissue. First, it was impossible to observe the extent of the frozen region during cryosurgery, and second there was no good understanding of the mechanism by which tissue is destroyed during freezing. Consequently, cryosurgery was typically used for treatment of disease in easily accessible areas where the extent of the frozen tissue could be observed visually. Furthermore, since the process of freezing was associated with damage to tissue, it was assumed that the lower the temperature to which the tissue is frozen, the greater the chances for destruction of the tissue. Therefore, the standard prior art approach to cryosurgery was to expose the tissue to as low a temperature as possible. More particularly, it was assumed that lowering the temperature of the tissue to $-50$ degrees C. would ensure the destruction of the tissue. The existing devices for cryosurgery reflect this particular state of knowledge.

The prior art devices are, in general, of the spray type, wherein the cold refrigerant is sprayed directly onto the tissue to be destroyed, or the closed end cryotip type, in which the refrigerant is delivered to a portion of the tip that is inserted in the tissue to be necrosed. Apparatus described in U.S. Pat. No. 4,376,376 issued to Gregory is exemplary of the spray type devices. The device described in U.S. Pat. No. 4,211,231 is exemplary of the closed end cryotip devices. Typical to all the prior art devices, which were developed in response to the known science at that time, is the fact that the extent of the freezing region is not controlled accurately because there was no way to observe the dimension of the tumor and of the tumors deep in the body. Therefore, an accurate control would not have been useful in any event. Also, the prior art systems were designed to achieve the lowest possible temperature on the tip, as fast as possible, to ensure that as much of the tip as possible is frozen to as low a temperature as possible.

Two major new advances were made recently in the area of cryosurgery. They are reviewed in the paper by Rubinsky and Degg, Proc., R. Soc. Lond. B234, 343-358 (1988). It was found that ultrasound can be used intraoperatively to determine, in real time, the extent of the tumors, as well as that of the frozen tissue during cryosurgery. Ultrasound works by sensing a pressure wave from a pressure transducer. The wave is reflected from boundaries between regions that have differences in acoustic impedance such as between tumors and normal tissue, blood vessels and tissue and frozen and unfrozen tissue. The reflected wave is identified by the pressure transducer and the extent of the tumor, or of the frozen region, is shown on a monitor. Following computerized interpretation of the data, this procedure facilitates an accurate identification of the extent of the tumor and of the frozen region during cryosurgery. Also, recent experiments described in the previously mentioned article by Rubinsky and Degg, have shed new light on the process of freezing in tissue. The results show that freezing in tissue is strongly affected by the structure of the tissue. Ice does not form uniformly throughout the tissue. Rather, it was shown that ice forms first in the blood vessels, while the cells surrounding the frozen blood vessels remain unfrozen. The rejection of saline during the freezing of the blood vessels causes an increase in the saline concentration in the solution inside the blood vessels. This causes water to leave the unfrozen cells through the cell membrane into the blood vessel. The consequent expansion of the blood vessels leads to the destruction of the vessels. Apparently the destruction of the frozen tissue is promoted by the fact that during freezing the vasculature network is destroyed and, therefore, cancerous and other nondesirable cells in the region that has been frozen are deprived of their blood supply after thawing and die because of ischemic necrosis. It was shown in the same paper that tissue can be destroyed by freezing to temperatures as high as $-2$ degrees C., and that temperatures as low as $-50$ degrees C. are not required for tissue destruction if the freezing process is done in such a manner as to ensure the destruction of the vasculature network. Destruction of the vasculature network can be achieved by varying the temperature of the cryosurgical tip in a predetermined controlled way. It is this aspect of cryosurgery to which the apparatus of the present invention is directed.

To summarize the new developments: (a) it is now possible to identify accurately both the tumor deep in the body and to observe, in real time, the extent of the frozen region; and (b) it has been established that a more efficient method of cryosurgery can be achieved by varying the temperature of the cryosurgical probe in a controlled way to ensure the destruction of tissue. These new developments can be compared to the previous state of the art in which, (a) it was impossible to determine accurately the tumor and the frozen region deep in the tissue; and (b) it was taught that to insure the destruction of the tissue, it is necessary to cool the tissue as fast as possible and to temperatures as low as possible. Consequently, the previous cryosurgical devices were designed in such a way that, (a) no importance was given to the exact extent of the frozen region because there was no way to know how much tissue is frozen during cryosurgery, or whether the whole tumor was frozen; and (b) the device was designed to deliver as much cooling power as possible locally to freeze the tissue to a temperature as low as possible without any concern being given to control over the temperature history during freezing.

SUMMARY OF THE INVENTION

It is an object of the present invention to provide a method and apparatus for cryosurgery which will enable precise control over the extent of the freezing of tissue in such a way that only the nondesirable tissue is frozen. More particularly, it is an object of the invention to provide an apparatus which enables precise control over the thermal history of the cryosurgical probe to facilitate freezing of the tissue in a manner to insure the efficient destruction of the non desirable tissue.

It is another object of the present invention to provide an apparatus of the aforementioned character in which several differently configured probes can be operated simultaneously with independent control.

Another object of the invention is to provide a cryoprobe having replaceable cryosurgical tips that can be exchanged rapidly so as to provide the best fit with the shape and location of the tumor as seen on intraoperative imaging devices (ultrasound).

Another object of the invention is to provide a cryoprobe having strategically located, low power electrical heaters which provide a mechanism for confining the freezing to desired active areas.

Still another object of the invention is to provide a cryoprobe of unique design in which a special fluid flow pattern is generated inside the active tip of the cryoprobe by means of a multiplicity of high thermal conductivity spheres disposed within the tip to insure a uniform tip temperature.

Yet another object of the invention is to provide an apparatus for cryosurgery which enables precise control over the thermal history of the tip by means of control over low power electrical heaters provided proximate the tip and by means of simultaneous control over the flow of low temperature fluids through the tip. Such control is accomplished in a way that the compensating effect of cooling by the refrigerant and heating by the heating elements is adjusted to achieve positive control over the thermal history in the probe.

DESCRIPTION OF THE INVENTION

Figure 1:
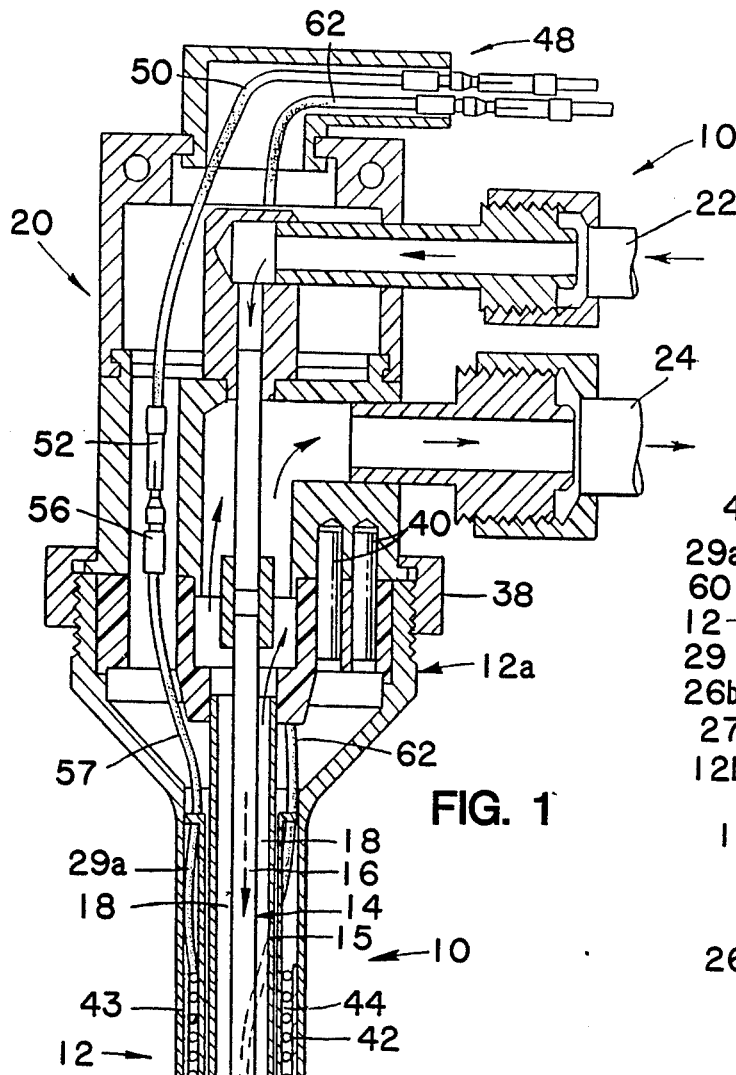
FIG. 1 is a side elevational, cross sectional view of the cryosurgical probe of the present invention.

Referring to the drawings, and particularly to FIGS. 1 through 4, one form of cryosurgical probe of the invention, and one form of control system of the invention embodying the probe (FIG. 4) is thereshown. The cryoprobe, generally designated by the numeral 10, comprises a tubular central housing 12 having a first upper end 12a and a second lower end 12b. Carried within housing 12 is a fluid inlet tube 14 which, along with a concentric central tube 15, defines longitudinally extending fluid inlet and outlet passages 16 and 18 respectively.

Connected to housing 12, proximate the first upper end 12a thereof, is a supply head assembly 20. Supply head assembly 20 has a cooling fluid inlet 22 in communication with inlet passageway 16 of housing 12 and an exhaust passageway 24 in communication with outlet passageways 18 of housing 12.

Figure 3:
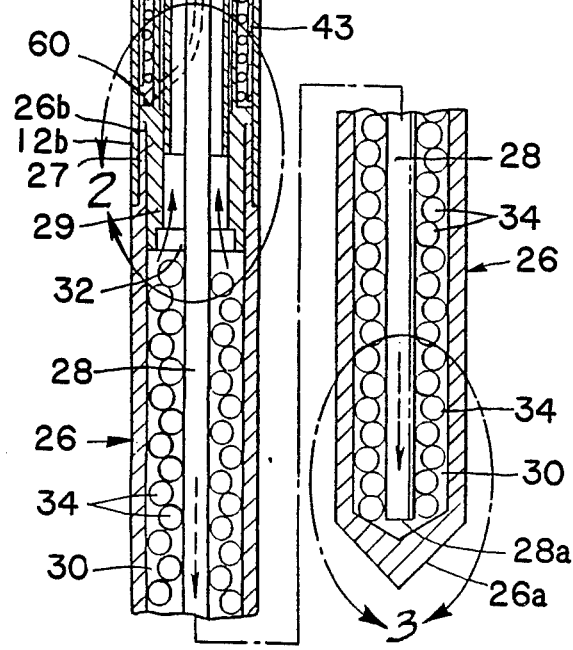
FIG. 3 is a greatly enlarged cross sectional view of the area designated in FIG. 1 by the numeral 3.
Figure 3:
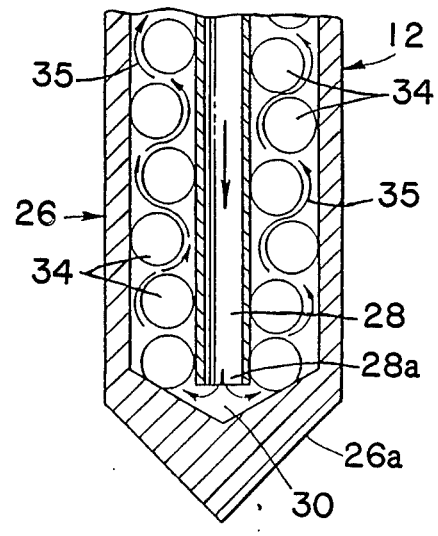

Referring also to FIG. 3, a freezing tip 26 is removably connected to housing 12 proximate its second or lower end 12b. Freezing tip 26 is closed at its lower end 26a to define an expansion chamber 30 and is connected at its opposite end 26b to the second end 12b of housing 12. Freezing tip 26 is coaxially aligned with fluid inlet tube 14 which defines a supply passageway 28 extending longitudinally of the freezing tip. Supply passageway 28 has an open end 28a disposed proximate expansion chamber 30 and in communication therewith. At its opposite, or upper, end, supply passageway 28 is in communication with fluid inlet passageway 16 which is defined by inlet tube 14. Proximate the upper end of freezing tip 26 are exhaust passageways 32 which are in communication with expansion chamber 30 and also with outlet passageways 18 of housing 12.

A highly important feature of the present invention comprises means disposed within expansion chamber 30 for interaction with cooling fluids flowing therethrough for enhancing heat transfer within the expansion chamber and for providing a circuitous cooling fluid flow path through the expansion chamber. In the embodiment of the invention shown in the drawings, these means comprise a multiplicity of discrete spherical members 34 disposed in a spaced apart relationship axially of exhaust chamber 30. As best seen in FIG. 3, members 34 define a circuitous path through the expansion chamber as indicated by the arrows 35. Members 34 are shown in the drawings as being spherical. It to be understood, however, that the members may take on any shape desirable for customizing the fluid flow characteristics and, concomitantly, the cooling characteristics of the freezing tip.

As will be discussed in greater detail hereinafter, members 34 can be constructed from a wide variety of different materials and can be formed in numerous configurations to enable full customizing of the cooling characteristics of the freezing tip. For example, members 34 may be constructed of a high thermal conductivity material such as copper or silver or they may be constructed of a lower thermal conductivity material such as teflon or nylon. It is apparent that through selection of the material from which members 34 are constructed, different cooling characteristics can be achieved as the liquid nitrogen flows into the expansion chamber and is gasified to cool the outer surfaces of the freezing tip. Depending upon the particular surgery being performed, the surgeon can predetermine the ideal temperature characteristics of the freezing tip (see for example, FIG. 5) and select a probe assembly, or tip, which will to provide the configuration, thermal conductivity and the circuitous path configuration optimum for providing the temperature desired at the exterior surfaces of the freezing tip.

Figure 2:
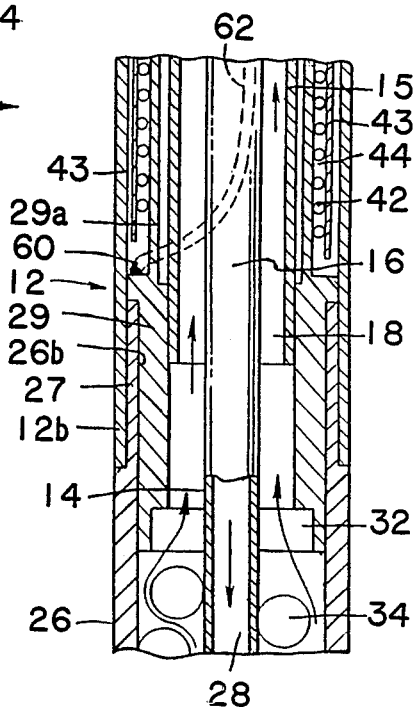
FIG. 2 is an enlarged cross sectional view of the area designated in FIG. 1 by the numeral 2.

Referring to FIG. 2, the freezing tip 26 is normally made of a high thermal conductivity material such as copper or silver. At the upper, or open, end 26b of the freezing tip, there is provided a reduced diameter portion designated in FIG. 2 by the numeral 27. This reduced diameter portion 27 is closely receivable within the lower, or second, end 12b of housing 12. By carefully dimensioning the component parts, a tight press fit seal can be achieved between the housing 12 and the freezing tip 26. Disposed internally of the junction of housing 12 and tip 26 is a freezing tip insert 29 which assists in the alignment and interconnection of the parts.

Referring again to FIG. 1, the upper end 12a of housing 12 is threaded so that the supply assembly 20 can be threadably interconnected thereto by means of an internally threaded connector ring 38. Alignment pins 40 are provided to ensure proper indexing of the supply head to the housing 12.

Forming another important aspect of the probe of the present invention is heater means for controllably heating selected portions of the freezing tip. In the present embodiment of the invention, this heater means is provided in the form of a heater element 42 (FIG. 1) which is disposed within an internal chamber 44 provided in housing 12 and defined by the outer wall of the housing and an inner concentric skirt portion 29a which extends upwardly from freezing tip insert 29. Heater element 42 is coil shaped and may be constructed of a nickel alloy or other suitable electrically resistive material. Preferably a thin film insulation material 43 is placed around the heater element 42.

Provided at the upper end of the supply head 20 is an electrical connector assembly 48 to which one end of an electrical conductor 50 is connected. The opposite end of conductor 50 is interconnected with a female connector 52 which, in turn, is connected to a male connector 56. Male connector 56 is electrically interconnected with heater element 42 by means of an electrical conductor 57 which extends downwardly through housing 12.

Heater element 42 is strategically positioned within housing 12 and accomplishes several important functions. First, in a manner presently to be described, it, along with the fluid flow control means of the invention, permits precise control of the temperature of the probe. Second, it supplies energy to prevent undesirable freezing of tissue to the housing. Third, on demand, it supplies energy to the freezing tip to free the tip from tissue which has been frozen during treatment. At the same time, heat supplied by the heater element functions to cauterize blood vessels in the proximity of the housing. Finally, the heating element supplies energy to the exhaust gas flowing through the housing to warm the supply head for surgeon comfort.

To permit precise control of the heating coil, or element 42, a temperature sensor 60, is provided within housing 12 at a selected strategic location depending upon the nature of the surgery to be performed. The sensor is shown here as being located proximate the lower extremity of the heating coil 42. As indicated in FIG. 1, the sensor lead wires 62 are entrained through the housing 12 and supply head 20 and exit the unit through the electrical connector assembly 48. The sensor 60 and the heating coil 42 are operably associated with a heater control means for precisely controlling the operation of the heater means. The details of the construction, installation and operation of the heater element, the temperature sensor and the heater control means is well known to those skilled in the art.

The heater control means of the invention forms a part of the broader control means of the invention which also includes a fluid flow control means for controlling the flow of liquid nitrogen to the probe. In a manner presently to be described, the control means functions to precisely control the heating and cooling of the freezing tip of the cryoprobe. The control means also includes a microprocessor means into which predetermined temperature control regimen programs can be inputted so that each probe being used during a particular surgery can be independently controlled in a prescribed manner. The microprocessor means can take several forms, but a commercially available computer such as that manufactured and sold by Energline Corporation under the name and style MULTITASKING has proven satisfactory for the present application. In addition to controlling the heater means and the fluid flow control means, the control means of the invention is capable of recording all relevant data chosen interactively by the user, for example, temperatures, durations, alarms and the like. The monitored data can be stored in the computer for later reference or can be outputted to a printer which is interconnected with the computer.

Figure 5:
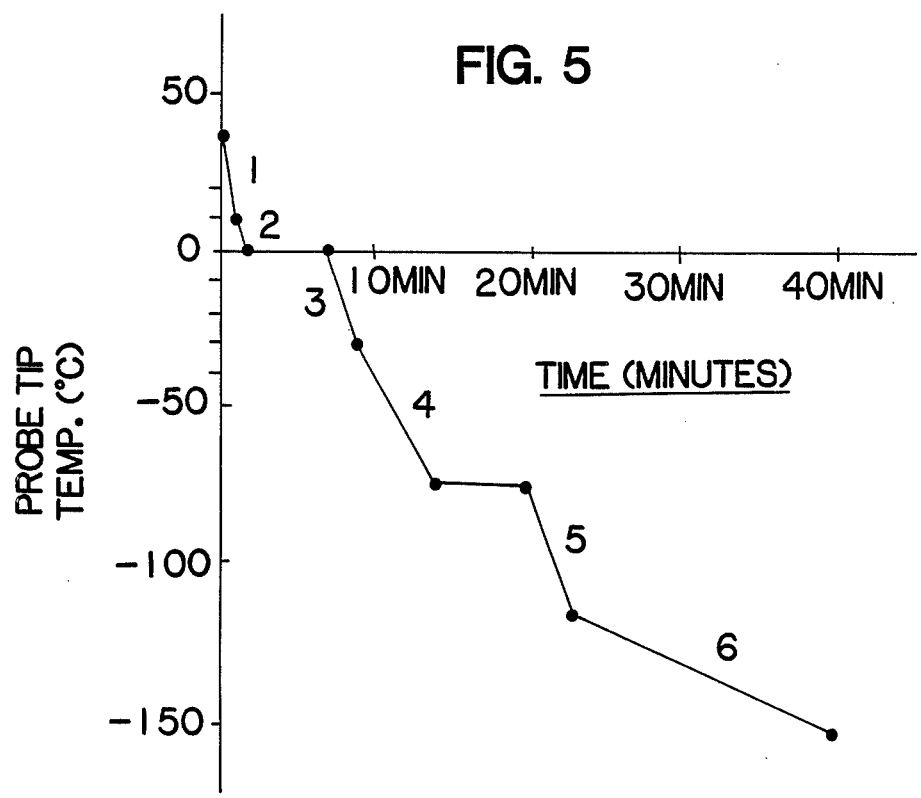
FIG. 5 is a diagrammatic view illustrating a sample cooling regimen of the cryoprobe.

Turning now to FIG. 5, the control means of the invention basically functions to permit the surgeon to input a predetermined, desired cooling curve, or regimen, for a particular surgery. This feature can be implemented by dividing the freezing process into several cooling segments. Each cooling segment is specified by its initial temperature (°C.), its ending temperature (°C.), its cooling rate (°C./Sec or °C./Min) and the way in which the cooling proceeds once the ending temperature is achieved. For example, as indicated in FIG. 5, segment No. 4 is specified by the following parameters: Start Temp=−30° C., Ending Temp=−75° C., Cooling Rate=9 degrees/minute, Transition=Manual. As illustrated in FIG. 5, if a manual transition is selected, the system controls the probe until it reaches the ending temperature and it would maintain the temperature constant until the user issues a command to proceed with the freezing process. Automatic transition simply indicates proceeding automatically to the next segment once the temperature reaches the ending temperature. Segments 3 and 5 are terminated with an automatic transition. In a manner well known to those skilled in the art, several different control modes can be implemented by the computer including automatic freezing, manual freezing and automatic thawing. The design of the control means is such that the surgeon can select the desired operating mode by a single key press. When multiple probes are used in a particular surgery, each of the cryosurgical probes operates independently from the rest allowing it to be operated in any desired operating mode and temperature regimen.

During the automatic freezing process, the control system continuously controls the probe temperature in order to accurately follow the particular cooling curve selected by the user. In this mode of operation, the probe temperature setpoint is continuously updated according to the preselected cooling curve. More particularly, the probe temperature is controlled to the desired temperature setpoint by implementing a P-I algorithm (Proportional & Integral action).

Figure 6:
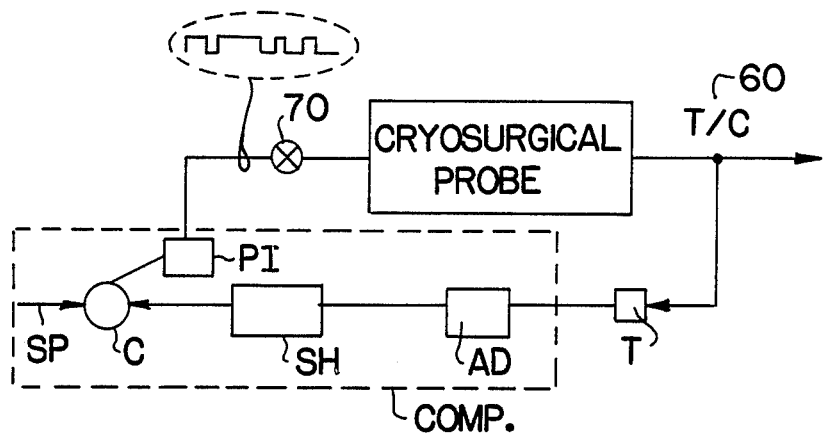
FIG. 6 is a generally schematic view illustrating one form of control system of the apparatus of the invention.

A schematic of the control system of one embodiment of the invention is depicted in FIG. 6. In FIG. 6, the element labeled T/C represents the sensor, or T-Type thermocouple 60 which is carried within housing 12 of the probe. The thermocouple signal from sensor 60 is amplified and conditioned by an accurate, optically isolated, thermocouple transmitter T. At this point the signal is transmitted to the computer, generally designated as Comp., and is converted into digital form by the computer's Analog to Digital Converter A/D. Next, the digital temperature reading is sampled at specified time intervals (for example, every 5 seconds) by the Sample Hold algorithm in the computer designated in FIG. 6 as SH. At every sampling interval the temperature is compared with the setpoint SP by a comparator C. The result of the comparison is used to compute the P-I algorithm PI for the next change in duty cycle to cooling control valve 70 (see also FIG. 4). In the manner earlier described, the freezing control valve modulates the flow of liquid nitrogen into the cryosurgical probe. Note that the results of the P-I algorithm is in the form of pulse width modulation (shown schematically in FIG. 6 and identified as PWM) where the controlled variable is the time during which liquid nitrogen is allowed to flow into the probe.

At the same time the flow of liquid nitrogen to the probe is being controlled by the control means, the control means is also controlling the heating element 42 which is housed within the probe. More particularly the heater element is appropriately regulated to maintain constant temperature in the upper cylindrical part of the cryosurgical probe. The heater element is also controlled using P-I action with the only difference being that the controlled variable is the heater ON/OFF time.

At any point during the automated freezing process the surgeon can override the preprogrammed curve and implement an alternative freezing strategy. In the manual freezing mode the control system continues to implement P-I temperature control except that the desired setpoint is set by the surgeon using an adjustable rotary knob.

Automatic thawing is accomplished in a similar manner as automatic freezing and the temperature is controlled to a preselected thawing curve. When it is desired to maintain a particular temperature, the control means will, on command, memorize the selected temperature and will control the probe to maintain this temperature.

The actual construction and programming of the computer control system described in the preceding paragraphs is well understood by those skilled in the art. All of the components necessary to implement the system, as shown in FIG. 6, are readily commercially available and their interconnection to cooperate in the manner described herein is well understood.

OPERATION

Before commencing the cryosurgery, the surgeon will typically study the location, depth and configuration of the diseased tissue using ultra sound techniques. Based upon this study, one or more appropriately configured cryoprobes will be chosen. A temperature curve, or regimen, will then be selected, or developed, for each probe and will be inputted into the computer. Alternatively, the surgeon may elect to control temperatures manually in the manner previously described. In either case, the control means, through cooperative interaction between the fluid flow control means and the heater control means, will precisely regulate the temperature of the probes being used, so as to freeze the undesirable tissue in the most efficient manner possible.

Figure 4:
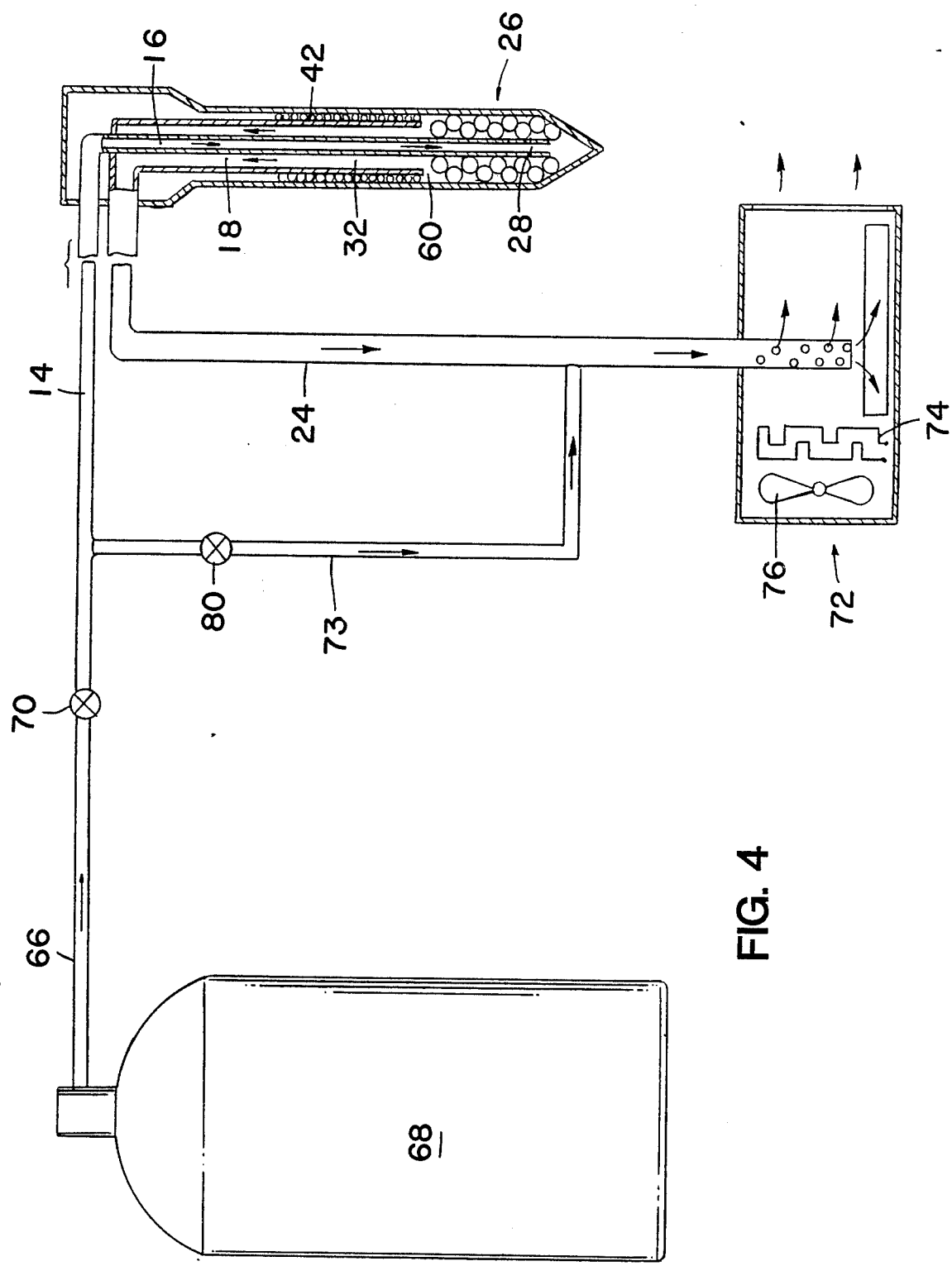
FIG. 4 is a generally diagrammatic view of the cryosurgery apparatus of the invention.

Referring to FIG. 4, the basic operation of the apparatus of the embodiment of the invention shown in the drawings is as follows: with the control strategy appropriately inputted to the computer in the manner described in the preceding paragraphs, the fluid flow control means will cause liquid nitrogen, at a temperature of approximately minus 325 degrees F. and at a predetermined pressure of about 35 p.s.i., to flow into a conduit 66 from a dewar 68 containing the liquid nitrogen. Conduit 66 is connected with a solenoid valve 70 which, in turn, is connected to supply tube 14. Solenoid valve 70 forms a part of the previously identified fluid flow control means. When valve 70 is open the liquid nitrogen flows through the supply tube, through the inlet passageway 16 and thence into the supply passageway 28 of the tip 26. As the liquid nitrogen flows from passageway 28 into the expansion chamber 30, it will boil and extract heat from both the tip and all the tissue in contact with the tip. Next, the nitrogen flows back through the instrument via exhaust passageways 32 and 18 and then outwardly from the unit through outlet 24. Preferably outlet 24 is interconnected with a liquid nitrogen evaporator 72 which includes a heater 74 and fan 76 to evaporate the remaining the liquid nitrogen.

When valve 70 is open a portion of the liquid nitrogen can also flow through a bypass conduit 73. A solenoid valve 80, which also forms a part of the fluid flow control means, is provided in conduit 73 to control the flow of liquid nitrogen through conduit 73. In normal operation, valve 80 is closed and the flow to the probe is regulated by solenoid valve 70. However, during initial cool down, where rapid cooling is desired, both valve 70 and 80 are open. As previously mentioned, in many prior art devices the liquid nitrogen used as the cooling medium becomes entrained in the resulting gas flow and exits the instrument through the exhaust tube without maximization of its cooling potential. In the apparatus of the present invention, these cooling potential losses are minimized by passing the liquid nitrogen through the matrix of high thermal conductivity spheres 34 and along the circuitous path designated by the arrows 35 in FIG. 3. The matrix increases the heat transfer area and the circuitous path defined by the matrix breaks up the gas/liquid flow to produce maximum gasification and concomitant cooling.

Upon completion of the surgery, the control means stops the flow of liquid nitrogen to the probe and appropriately controls the heating coil to permit the expeditious removal of the cryotip from the proximity of the tissue.

It is to be noted that only one probe is shown in FIG. 4. In practice several probes can be interconnected with the source of liquid nitrogen and precisely controlled by the control means in the manner previously described herein. The several probes used can be of varied configuration to meet the needs of the particular surgery.

As previously discussed, when it is desired to vary the configuration or temperature characteristics of a particular probe, the housing and tip assembly can quickly and easily be removed from the supply head and replaced with an assembly of a different, more convenient configuration. For example, an assembly can be selected wherein the spherical members are of a different material and, if desired, of a different size and configuration. More particularly, instead of using a high thermal conductivity material such as silver for the spheres 34, lower thermal conductivity material such as stainless steel might be advantageous for certain types of treatment. In practice, the doctor can take into the operating room an assortment of tip and housing assemblies of various external shapes and internal configurations having differing characteristics so that the optimum assembly can be quickly selected and used.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for cryosurgery comprising:
   a. a source of low temperature cooling fluid;
   b. at least one cryosurgical probe having:
      (1) a housing having first and second ends and fluid inlet and outlet passageways extending therethrough, said fluid inlet passageway being in communication with said source of low temperature cooling fluid;
      (2) a freezing tip closed at one end to define an expansion chamber and being removably connected at its opposite end to said housing, said freezing tip having:
         (a) a supply passageway having an open end disposed proximate said expansion chamber of said freezing tip and being in communication at its opposite end with said fluid inlet passageway of said housing; and
         (b) an exhaust passageway in communication with said expansion chamber and with said outlet passageway of said housing; and
      (3) heater means for controllably heating selected portions of said freezing tip and said housing; and
      (4) sensor means for sensing the temperature of selected portions of said freezing tip and said housing;
   c. control means for precisely controlling the heating and cooling of said cryosurgical probe in accordance with a desired temperature regimen, said control means including:
      (1) fluid flow control means operably associated with said cryosurgical probe for controlling the flow of fluid from said source of low temperature cooling fluid to said cryosurgical probe; and
      (2) heater control means operably associated with said sensor means and said heater means for controlling said heater means, said heater means operating in cooperation with said fluid flow control means to control the rate and degree of cooling of said cryosurgical probe.

2. An apparatus as defined in claim 1 in which said heater means comprises an electrically energized heating element carried within said housing.

3. An apparatus as defined in claim 1 in which said control means is adapted to control the heating and cooling of said cryosurgical protein accordance with a predetermined temperature regimen.

4. An apparatus as defined in claim 3 in which said control means further includes microprocessor means operably associated with said sensor means, said fluid flow control means and said heater control means for receiving a plurality of temperature regimen programs and, on command, selectively controlling said fluid flow control means and said heater control means to heat and cool said cryosurgical probe in accordance with a selected, predetermined temperature regimen.

5. An apparatus as defined in claim 4 further including means disposed within said expansion chamber for interaction with cooling fluids flowing therethrough for enhancing heat transfer in a manner to uniformly cool said freezing tip and to minimize cooling potential losses.

6. An apparatus as defined in claim 5 in which said means disposed within said expansion chamber comprises a multiplicity of discrete members disposed in a spaced apart relationship within said expansion chamber for increasing the heat transfer area along the path of flow of the cooling fluid.

7. An apparatus for cryosurgery comprising:
   a. a source of liquid nitrogen;
   b. at least one cryosurgical probe having:
      (1) a housing having first and second ends and fluid inlet and outlet passageways extending therethrough, said fluid inlet passageway being in communication with said source of liquid nitrogen;
      (2) a freezing tip closed at one end to define an expansion chamber and being removably connected at its opposite end to said housing, said freezing tip having:
         (a) a supply passageway having an open end disposed proximate said expansion chamber of said freezing tip and being in communication at its opposite end with said fluid inlet passageway of said housing;
         (b) an exhaust passageway in communication with said expansion chamber and with said outlet passageway of said housing; and
         (c) a plurality of discrete spheres disposed within said expansion chamber for interaction with cooling fluids flowing therethrough for enhancing heat transfer in a manner to uniformly cool said freezing tip;
      (3) heater means for controllably heating selected portions of said freezing tip and said housing; and
      (4) sensor means for sensing the temperature of selected portions of said freezing tip and said housing;
   c. control means for precisely controlling the heating and cooling of said cryosurgical probe in accordance with a predetermined temperature regimen, said control means including:
      (1) fluid flow control means operably associated with said cryosurgical probe for controlling the flow of fluid from said source of low temperature cooling fluid to said cryosurgical probe; and
      (2) heater control means operably associated with said sensor means and said heater means for controlling said heater means.
      (3) microprocessor means operably associated with said sensor means and with said fluid flow control means and said heater control means for receiving a plurality of temperature regimen programs for controlling said fluid flow control means and said heater control means to heat and cool said cryosurgical probe in accordance with a selected temperature regimen.

8. An apparatus as defined in claim 7 in which said fluid flow control means comprises a first conduit connecting said source of liquid nitrogen with said cryosurgical probe, a second bypass conduit connected to said first conduit and first and second valves for controlling the flow of liquid nitrogen through said first and second conduits.

* * * * *

UNITED STATES PATENT AND TRADEMARK OFFICE
CERTIFICATE OF CORRECTION

PATENT NO. : 4,946,460

DATED : August 7, 1990

INVENTOR(S) : Merry, et al.

It is certified that error appears in the above-identified patent and that said Letters Patent is hereby corrected as shown below:

Column 9 line 67;
Claim 3, line 3, delete "protein", insert --probein--.

Signed and Sealed this

Twenty-first Day of July, 1992

Attest:

DOUGLAS B. COMER

*Attesting Officer*  *Acting Commissioner of Patents and Trademarks*